United States Patent [19]
Ku

[11] Patent Number: 5,837,829
[45] Date of Patent: Nov. 17, 1998

[54] 9-OXIMESILYL ERYTHROMYCIN A DERIVATIVES

[75] Inventor: Yi-Yin Ku, Buffalo Grove, Ill.

[73] Assignee: Abbott Laboratories, Abbott Park, Ill.

[21] Appl. No.: 626,524

[22] Filed: Apr. 2, 1996

[51] Int. Cl.⁶ .............................. C07H 1/00; C07H 17/08
[52] U.S. Cl. ........................... 536/7.4; 536/7.2; 536/18.5; 536/18.6
[58] Field of Search ........................ 536/7.2, 7.4, 18.6, 536/18.5

[56] References Cited

U.S. PATENT DOCUMENTS

| | | | |
|---|---|---|---|
| 4,640,910 | 2/1987 | Faubl et al. | 514/29 |
| 4,990,602 | 2/1991 | Morimoto et al. | 536/7.4 |

FOREIGN PATENT DOCUMENTS

| | | |
|---|---|---|
| 0195960 A | 10/1986 | European Pat. Off. . |
| 0260938 A | 3/1988 | European Pat. Off. . |
| 0272110 A | 6/1988 | European Pat. Off. . |

OTHER PUBLICATIONS

Journal of Antibiotics, vol. 46, No. 4 (Apr. 1993) pp. 647–660, Y.Watanabe et al., "Chemical Modification of Erythromycins. IX".

*Primary Examiner*—Elli Peselev
*Attorney, Agent, or Firm*—Mona Anand

[57] ABSTRACT

A process of preparing 6-O-alkylerythromycin A using 9-oximesilyl erythromycin A derivatives is provided. 9-Oximesilyl- and 6-O-alkylerythromycin A derivatives used in the preparation of 6-O-alkylerythromycin A are also provided.

9 Claims, 1 Drawing Sheet

＃ 9-OXIMESILYL ERYTHROMYCIN A DERIVATIVES

DESCRIPTION

1. TECHNICAL FIELD OF THE INVENTION

The present invention relates to erythromycin derivatives. More particularly, the present invention pertains to erythromycin A 9-oximesilyls and their use in the production of 6-O-alkyl erythromycin A derivatives.

2. Background of the Invention

6-O-alkyl derivatives of erythromycin A have use as antibacterial agents. For example, 6-O-methylerythromycin A (clarithromycin), shown below, is a potent macrolide antibiotic (U.S. Pat. No. 4,331,803).

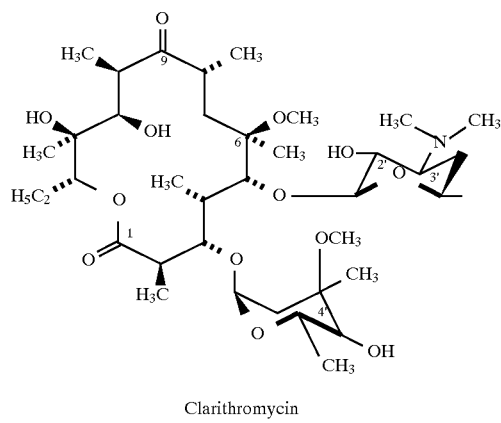

Clarithromycin

A variety of processes for preparing 6-O-methylerythromycin A have been described. 6-O-methylerythromycin A can be prepared by methylating a 2'-O-3'-N-dibenzyloxycarbonyl-des-N-methyl derivative of erythromycin A (U.S. Pat. No. 4,331,803). 6-O-methylerythromycin A can also be made from 9-oxime erythromycin A derivatives (See, e.g., U.S. Pat. Nos. 5,274,085; 4,680,386; 4,668,776; 4,670,549 and 4,672,109 and European Patent Application 0260938 A2).

When 9-oxime erythromycin A derivatives are utilized, the oxime is protected during methylation with a 2-alkenyl group (U.S. Pat. Nos. 4,670,549 and 4,668,776), a benzyl or substituted benzyl group (U.S. Pat. Nos. 4,680,386, and 4,670,549) or a moiety selected from the group consisting of lower alkyl, substituted alkyl, lower alkenyl, aryl substituted methyl, substituted oxalkyl, and substituted thiomethyl (U.S. Pat. No. 4,672,109). However, when the oximes are protected with a trimethylsilyl group, they are too unstable during methylation under alkaline conditions. (J. of Antiobiotics, Vol. 46, No. 6, p. 647,1993).

There are drawbacks to the existing methods for producing 6-O-methylerythromycin A. By way of example, failure to protect the 2'-OH group leads to undesired methylation of that group. Existing methods for protecting the 2'-OH group are unsatisfactory because those methods also require protection of the 3'-nitrogen. U.S. Pat. No. 4,680,386, for example, discloses protection of the 2'-OH group with a benzyloxy carbonyl moiety. Under such circumstances, however, the 3'-nitrogen also undergoes N-demethylation followed by N-benzyloxy carbonyl formation. This 3'-N-benzyloxy carbonyl group must be deprotected following 6-O-methylation. The 3'-dimethylamino group is regenerated following 6-O-methylation by N-methylation. U.S. Pat. No. 4,670,549 discloses protection of the 2'-OH group as a benzyl or like substituent. Under these circumstances, the 3'-nitrogen group must also be protected as a quaternary salt. This quaternary salt must be removed following 6-O-methylation to regenerate the 3'-dimethyl amino group. By way of further example, the use of benzyloxycarbonyl groups for protection of the 2'-hydroxy group (U.S. Pat. No. 4,311,803) requires large amounts of benzyl chloroformate, which is severely irritating and toxic. Deprotection of 9-oxime protected with oxyalkyls has to be carried out in harsh conditions, which lead to undesired side product formation.

There continues to be a need to provide a rapid, efficient method of producing 6-O-alkylerythromycin A that uses mild, neutral reaction conditions.

BRIEF SUMMARY OF THE INVENTION

The present invention provides an efficient and practical method of synthesizing 6-O-alkyl-erythromycin A derivatives. The synthetic process starts with a 9-oxime erythromycin A derivative which, by definition, includes a 6-hydroxy group. The derivative is converted to a 9-oximesilyl erythromycin A derivative, which is O-protected at the 2'-OH position and then selectively alkylated at the 6-oxygen. The 6-O-alkylated derivative is then desilylated and deoximated to give a 6-O-alkylerythromycin A.

The 9-oximesilyl erythromycin A derivative is prepared by reacting a 9-oxime erythromycin A derivative with a silylating agent to form an O-protected-oxime having a protecting group of the formula:

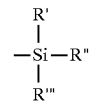

where R', R", and R'" are independently hydrogen, lower alkyl, aryl, phenyl, phenyl substituted lower alkyl, cycloalkyl or alkenyl.

A 9-oxime erythromycin A derivative used in a process of the present invention can be unsubstituted at the 2'-OH and 4'-OH positions or can contain a conventional O-protecting group at those positions. Exemplary and preferred O-protecting groups include silyl (SiR'R"R'", where R', R" and R'" are as defined above), acyl, lower alkenyl monocarbonyl, lower alkoxycarbonylalkylcarbonyl, and arylcarbonyl groups.

The 9-oxime derivative can also be unsubstituted at the 3'-dimethylamino position or can contain a convention N-protecting group at that position. Exemplary and preferred N-protecting groups are alkoxycarbonyl groups, alkoxyalkoxycarbonyl groups, haloalkoxycarbonyl groups, unsaturated alkoxycarbonyl groups, substituted benzyloxycarbonyl groups, substituted phenoxycarbonyl groups, and the like.

The present invention also relates to novel intermediates useful in the preparation of 6-alkylerythromycin A. Those intermediates are 9-oximesilyl derivatives that are alkylated at the 6-position and unsubstituted or substituted at the 2'-, 3'- and/or 4"- positions.

BRIEF DESCRIPTION OF THE DRAWINGS

In the drawings, which form a portion of the specification.

DETAILED DESCRIPTION OF THE INVENTION

Figure 1:
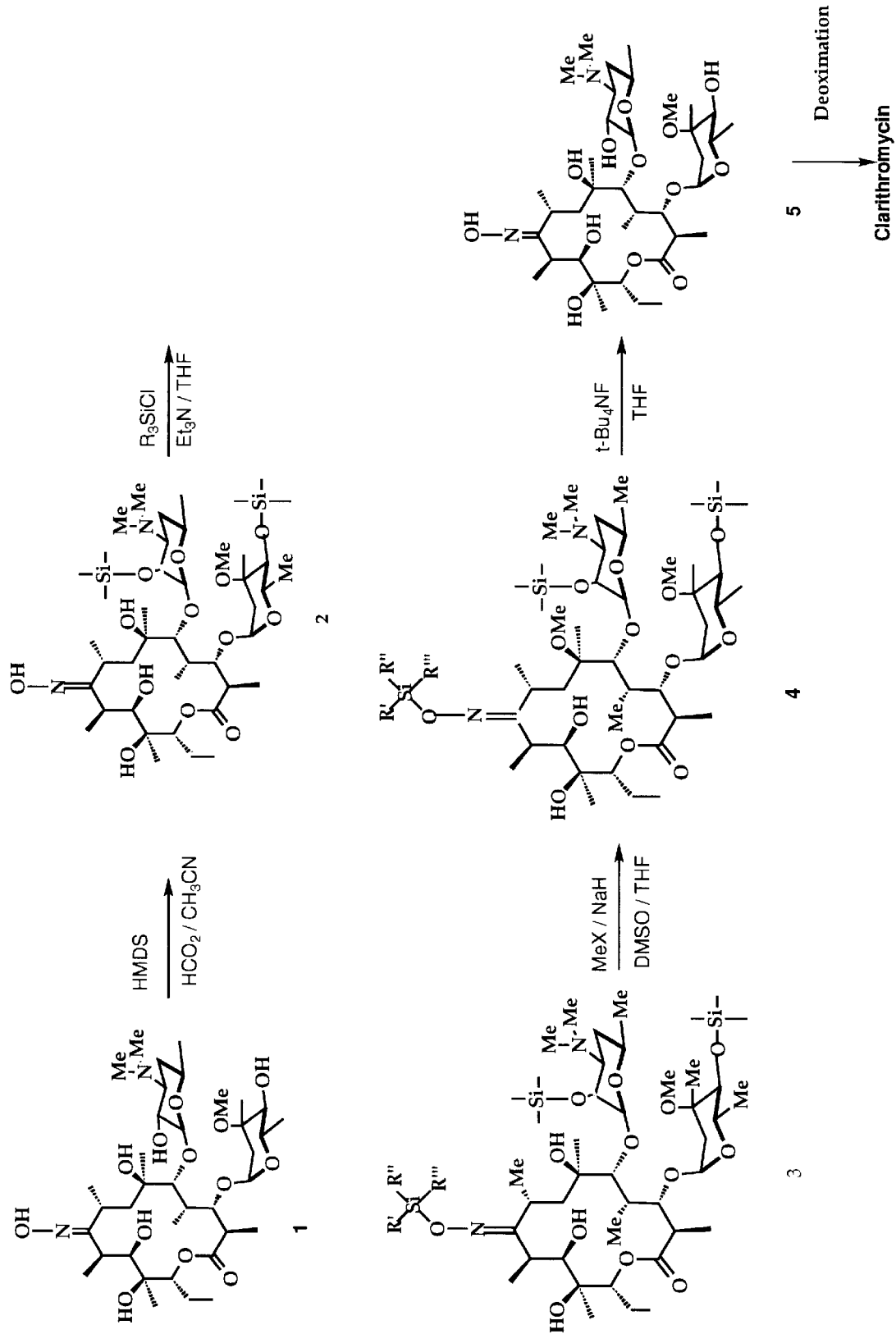
FIG. 1 shows one embodiment of a process of preparing 6-O-methyl erythromycin A.

In one aspect, the present invention provides a process of preparing a 6-O-alkyl derivative of erythromycin A. That process includes the steps of converting a 9-oxime erythromycin A derivative into a 9-oximesilyl erythromycin A derivative and reacting the 9-oximesilyl erythromycin A derivative with an alkylating agent.

A process of the present invention begins with a 9-oxime erythromycin A derivative. 9-Oxime derivatives are prepared using standard procedures well known in the art. Briefly, an erythromycin A derivative is reacted with either hydroxylamine hydrochloride and a base, free hydroxylamine in methanol or hydroxylamine and an organic acid (See, e.g., U.S. Pat. No. 5,274,085, the disclosure of which is incorporated herein by reference).

The 9-oxime erythromycin A derivative is silylated by reacting the derivative with a silylating agent. A preferred silylating agent has the formula

where R', R", and R'" are independently hydrogen, lower alkyl, aryl, phenyl, phenyl substituted lower alkyl, cycloalkyl or alkenyl and X is a halogen or a sulfonate (e.g., mesylate, tosylate). The silylating reaction is carried out in the presence of a suitable organic base such as triethylamine (Et$_3$N), pyridine, imidazole or di-trimethylsilyl amine [HN(TMS)$_2$].

Another exemplary silylating agent has the formula:

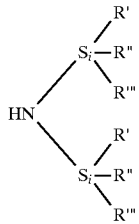

where R', R", and R'" are defined above. The silylating reaction can also be carried out in the presence of a suitable acid such as HCO$_2$H.

As is well known in the art, to efficiently and selectively alkylate erythromycin A at the 6-OH position, the hydroxyl groups at the 2'- and/or 4"-positions should be protected prior to methylation. It may also be desirable to protect the 3'-dimethylamino moiety. Such protection is accomplished by protecting those groups with conventional O- or N-protecting groups. The order of protection of 9-oxime and 2', 4"- OH groups can be exchanged.

A 9-oximesilyl erythromycin A derivative formed during a synthetic process of the present invention corresponds to the structure I, below:

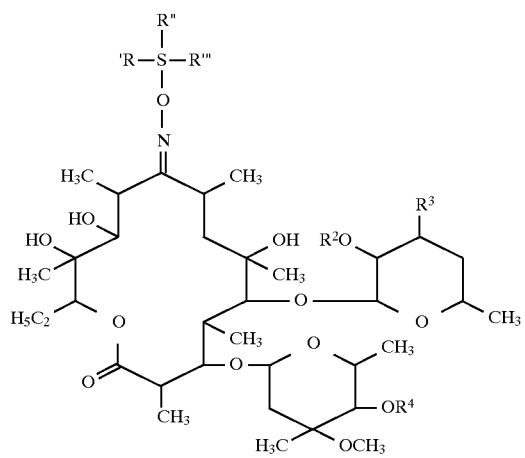

where R', R" and R'" are as defined above; R$^2$ and R$^4$ are each independently hydrogen or a conventional O-protecting group, R$^3$ is —NR$^5$CH$_3$, where R$^5$ is methyl (CH$_3$) or a conventional N-protecting group or —N$^+$(CH$_3$)$_2$R$^6$X$^-$, where R$^6$ is 2-alkenyl, benzyl or substituted benzyl, and X is a halogen such as Br, Cl or I.

The compound of structure I is shown without spatial bond orientation. Structure I, thus, defines all combinations of bond orientation and is intended to cover all possible stereo-configurations (e.g., epimers). In a preferred embodiment, the bond orientations of Structure I are the same as shown above for 6-O-methylerythromycin A.

In one embodiment, the 9-oxime erythromycin A derivative is unsubstituted (unprotected) at the 2'-, 3' and 4"-positions. Silylation of such a derivative results in formation of a 9-oximesilyl derivative of structure I, where R$^2$ and R$^4$ are both hydrogen and R$^3$ is methyl.

In another embodiment, the 9-oxime erythromycin A derivative used in the synthetic process has conventional O-protecting groups at the 2'- and 4"- positions. Conventional O-protecting groups for protecting hydroxyls from alkylation are well known in the art and include silyl, acyl, lower alkenyl monocarbonyl, alkoxycarbonyl, alkylcarbonyl, lower alkoxycarbonylalkylcarbonyl, and arylcarbonyl groups. Silylation of such a substituted 9-oxime erythromycin A derivative results in a 9-oximesilyl derivative of structure I, where R$^2$ and R$^4$ are silyl, carbonyl, acyl, alkoxycarbonyl, alkylcarbonyl, lower alkenyl monocarbonyl, lower alkoxycarbonylalkylcarbonyl, or arylcarbonyl.

Exemplary and preferred O-protecting groups are alkoxycarbonyls (e.g., methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl and the like), alkoxyalkoxycarbonyls (e.g., methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl and the like), haloalkoxycarbonyls (e.g., 2-chloroethoxycarbonyl, 2-chloroethoxycarbonyl, 2,2,2-tri-chloroethoxycarbonyl and the like), unsaturated alkoxycarbonyls (e.g., allyloxycarbonyl, pro-pargyloxycarbonyl, 2-butenoxycarbonyl, 3-methyl 2-butenoxycarbonyl and the like), substituted benzyloxycarbonyls (e.g., benzyloxycarbonyl, p-methylbenzyloxycarbonyl, p-methoxybenzyloxycarbonyl, p-nitro-benzyloxycarbonyl, 2,4-dinitrobenzyloxycarbonyl, 3,5-dimethylbenzyloxycarbonyl, p-chlorobenzyloxycarbonyl, p-bromobenzyloxycarbonyl and the like) and substituted phenoxycarbonyls [e.g., phenoxycarbonyl, p-nitrophenoxycarbonyl, o-nitrophenoxycarbonyl, 2,4-dinitrophenoxycarbonyl, p-methylphenoxycarbonyl, m-methylphenoxycarbonyl, o-bromophenoxycarbonyl, 3,5-dimethylphenoxycarbonyl, p-chlorophenoxycarbonyl, 2-chloro 4-nitrophenoxycarbonyl and the like (See, e.g., Greene and Wuts' *Protective Groups in Organic Synthesis*, 2d. Ed. John Wiley & Sons, Inc., New York, 1991., the disclosure of which is incorporated herein by reference).

Exemplary and preferred lower alkyl monocarbonyl groups are acetyl, propionyl, butyryl, isobutyryl and the like. Exemplary and preferred lower alkenyl monocarbonyl groups include acryloxyl, methacryloxy and the like. Exemplary and preferred lower alkoxycarbonyl-alkylcarbonyl groups include methoxycarbonyl-methylcarbonyl, ethoxycarbonylmethylcarbonyl, ethoxycarbonyl-ethylcarbonyl and the like. Exemplary and preferred arylcarbonyl groups include benzoyl, p-methoxybenzoyl, 3,4,5-trimethoxybenzoyl, p-chlorobenzoyl, 2,4-dichlorobenzoyl, 3,5-dichlorobenzoyl, diphenylacetyl, 1-naphthaleneacetyl, 2-naphthaleneacetyl and the like. Exemplary and preferred silyl groups have the formula:

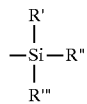

where R', R", and R'" are as defined above.

The use of O-protecting groups in the preparation of erythromycin derivatives has been described (See, e.g., U.S. Pat. No. 4,672,109, and European Patent Application 0260938A2, the disclosures of which are incorporated herein by reference).

Conventional O-protecting groups, as set forth above, are positioned using standard procedures well known in the art. By way of example, a trimethyl silyl group can be positioned at the 2'- and 4"-positions by reacting a 9-oxime erythromycin A derivative with the silylating agent hexamethyidisilane (HMDS) in the presence of acid (e.g., $HCO_2H$). This same transformation can be carried out using other silylating agents such as trimethylsilylchloride (TMSCl). in the presence of an organic base such as $Et_3N$, pyridine, or imidazole. Other silylation conditions can also be used.

An acetyl group can be positioned at the 2'- and 4"-positions by reacting an erythromycin A derivative (9-oxime or 9-oximesilyl) with an acetylating agent and a base. Suitable acetylating agents that can be used include anhydride and acid halide compounds of the formula $(R^5CO)_2O$ or $R^5COCl$, where $R^5$ is hydrogen or a substituent group such as lower alkyl (e.g., methyl, ethyl, n-propyl, isopropyl, n-butyl, sec-butyl, t-butyl and the like) or aryl (e.g., phenyl, p-methoxyphenyl, p-chlorophenyl, m-chlorophenyl, o-chlorophenyl, 2,4,-dichlorophenyl, p-bromophenyl, m-nitrophenyl, p-nitrophenyl, benzhydryl, 1-naphthyl and the like). Suitable bases are organic bases such as triethylamine, pyridine and diethylamine.

One of skill in the art will readily appreciate that it may be advantageous to also substitute for a methyl group of the dimethylamino moiety at the 3'-position of erythromycin A using a conventional N-protecting group. Exemplary and preferred N-protecting groups are alkoxycarbonyl groups (e.g., a methoxycarbonyl group, an ethoxycarbonyl group, an isopropoxycarbonyl group, an n-propoxycarbonyl group, an n-butoxycarbonyl group, an isobutyloxycarbonyl group, a sec-butyloxycarbonyl group, a t-butyloxycarbonyl group, a 2-ethylhexyloxycarbonyl group, a cyclohexyloxycarbonyl group, a methyloxycarbonyl group and the like); alkoxy-alkoxycarbonyl groups (e.g., a methoxymethoxycarbonyl group, an ethoxymethoxycarbonyl group, a 2-methoxyethoxycarbonyl group, a 2-ethoxyethylcarbonyl group, a 2-ethoxyethoxycarbonyl group, a 2-butoxyethoxycarbonyl group, a 2-methoxyethoxymethoxycarbonyl group and the like); haloalkoxycarbonyl groups (e.g., a 2-chloroethoxycarbonyl group, a 2-chloroethoxycarbonyl group, a 2,2,2-trichloroethoxycarbonyl group and the like), unsaturated alkoxycarbonyl groups (e.g., an allyloxycarbonyl group, a propargyloxycarbonyl group, a 2-butenoxycarbonyl group, a 3-methyl-2-butenoxycarbonyl group and the like), substituted benzyloxycarbonyl groups (e.g., a benzyloxycarbonyl group, a p-methylbenzyloxycarbonyl group, a p-methoxybenzyloxycarbonyl group, a p-nitrobenzyloxycarbonyl group, a 2,4-dinitrobenzyloxycarbonyl group, a 3,5-dimethylbenzyloxycarbonyl group, a p-chlorobenzyloxycarbonyl group, a p-bromobenzyloxycarbonyl group and the like), and substituted phenoxycarbonyl groups [e.g., a phenoxycarbonyl group, a p-nitrophenoxycarbonyl group, an o-nitrophenoxycarbonyl group, a 2,4-dinitrophenoxycarbonyl group, a p-methylphenoxycarbonyl group, an m-methylphenoxycarbonyl group, an o-bromophenoxycarbonyl group, a 3,5-dimethylphenoxycarbonyl group, a p-chloro-phenoxycarbonyl group, a 2-chloro-4-nitrophenoxycarbonyl group and the like (U.S. Pat. No. 4,672,109)].

The dimethylamino moiety at the 3'-position may also be protected as a quaternary salt by reacting it with a derivative R-X, wherein R is a 2-alkenyl group, a benzyl group or a substituted benzyl group; and X is a halogen atom (See, e.g., U.S. Pat. No. 4,670,549). The 9-oximesilyl, 2'- and 4"-substituted erythromycin A derivative is then selectively alkylated at the 6-position. Procedures and reagents for alkylating the 6-position of erythromycin A derivatives are well known in the art (See, e.g., U.S. Pat. Nos. 4,672,109 and 4,670,549).

Briefly, a compound of Structure I is reacted with a suitable alkylating agent in the presence of a base. Exemplary and preferred alkylating agents are methyl bromide, ethyl bromide, n-propyl bromide, methyl iodide, ethyl iodide, n-propyl bromide, dimethyl sulfate, diethyl sulfate, di-n-propyl sulfate, methyl-p-toluenesulfonate, ethyl methanesulfonate, n-propyl methanesulfonate and alkyl triflates.

Exemplary and preferred bases are a strong alkali metal base, preferably selected from the group consisting of an alkali metal hydride, alkali metal hydroxide or alkali metal alkoxide, and a weak organic amine base, preferably selected from the group consisting of trimethylamine, triethylamine, tripropylamine, pyridine, 2-methoxypyridine, 1-methylpyrrolidine, 1-methylpiperidine, and 1-ethylpiperidine.

The methylation step is carried out in a suitable solvent. Exemplary and preferred solvents are polar aprotic solvents such as N,N-dimethylformamide, dimethyl sulfoxide, N-methyl-2-pyrrolidone, hexamethylphosphoric triamide, tetrahydrofuran, 1,2-dimethoxyethane, acetonitrile, ethyl acetate or methyl-t-butyl ether, or a mixture of such polar aprotic solvents maintained at a reaction temperature and for a period of time sufficient to effect alkylation, preferably from −15° C. to room temperature for a period of 1 to 8 hours. The preferred solvent includes at least methyl-t-butyl ether.

Alkylation of the 6-position of a compound of structure results in formation of a compound of structure II, below:

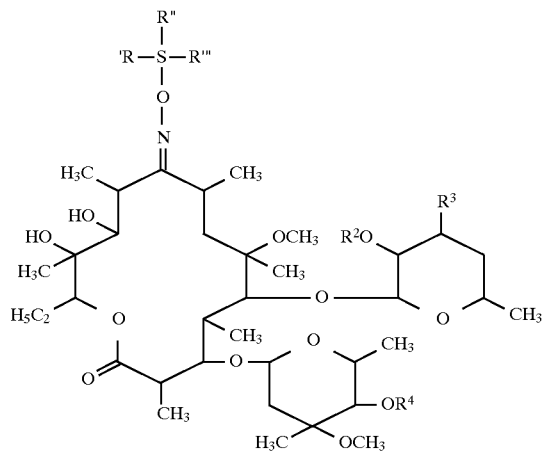

where R', R", R"', $R^2$, $R^3$ and $R^4$ are as defined above for structure I.

The preparation of 6-O-alkylerythromycin A proceeds by removing the O-protecting groups from the 2'- and 4"-positions and the silyl group from the 9-oximesilyl and then deoximating the 9-oxime. Means for removing the O-protecting groups at the 2'- and 4"-positions are well known in the art and depend upon the nature of the protecting group.

By way of example, where the 2' and/or 4"-positions are acetylated, the acetyl group can be removed by reacting the acetylated derivative with a compound of the formula $R^6OH$, where $R^6$ is alkyl (e.g., methyl, ethyl, propyl, isopropyl, n-butyl, sec-butyl, t-butyl and the like). The reaction can take place in the absence or presence of an acid (e.g., formic acid, acetic acid) or water, or can take place in the absence or presence of a base (e.g., $K_2CO_3$, $Na_2CO_3$, $KHCO_3$, $NaHCO_3$).

Where the 2' and/or 4"-positions are silylated, the silyl group can be removed by reacting the silylated derivative with formic acid ($HCO_2H$) in isopropyl alcohol (IPrOH). As is well known in the art, removal of the silyl group can also be accomplished using (a) $Bu_4NF$ in THF, (b) HOAc/THF/$H_2O$, (c) citric acid/MeOH, (d) Dowex resin/MeOH, $K_2CO_3$/MeOH, (e) n-$Bu_4NCl/KF$ or (f) HF/$CH_3CN$.

Removal of the silyl group from the 9-oximesilyl is accomplished using the same procedures as set forth above in relation to removal of the silyl group from the 2'- and/or 4"-positions. It is advantageous to use a silyl group for protection of the 2'- and 4"-positions because deprotection of those groups can occur in the same step as removal of the silyl group from the 9-oximesilyl. Still another advantage of using silyl groups is that deprotection (desilylation) can be accomplished using mild (room temperature), neutral conditions.

A final step in the preparation of a 6-O-alkylerythromycin A is deoximation. Deoximation is carried out in accordance with standard procedures well known in the art (See e.g., U.S. Pat. No. 4,672,109). Briefly, the 9-oxime derivative is reacted with sodium hydrogen sulfite in alcohol (e.g., ethanol) and refluxed. The solution is cooled, alkalinized and precipitated with aqueous sodium bicarbonate. The precipitate formed in the above reaction is collected by filtration, washed and recrystallized with alcohol.

A detailed description of the synthesis of 6-O-methylerythromycin A, using a process of the present invention is set forth hereinafter in the Examples. A schematic illustration of one embodiment of a synthetic scheme in accordance with the present invention is set forth in FIG. 1.

With reference to FIG. 1, a 9-oxime erythromycin A derivative (Compound 1) is reacted with hexamethyldisilazane (HMDS) in the presence of formic acid ($HCO_2H$) in acetonitrile ($CH_3CN$) to form a 2', 4"-bis-trimethylsilyl, 9-oxime erythromycin A derivative (Compound 2).

Compound 2 is then reacted with a silylating agent ($R_3SiCl$) in the presence of triethylamine ($Et_3N$) and tetrahydrofuran (THF) to form a 2', 4"-bis-trimethylsilyl, 9-oximesilyl erythromycin A derivative (Compound 3).

Methylation of the 6-OH is then carried out by reacting Compound 3 with a methylating agent (MeX) and sodium hydride (NaH) in an appropriate solvent [dimethylsulfoxide (DMSO) and THF] to form a 2', 4"-di-trimethylsilyl, 6-O-methyl, 9-oximesilyl erythromycin A derivative (Compound 4). The silyl groups at the 2', 4"- and 9-positions are removed by reacting Compound 4 with $Bu_4NF$ in THF to form a 2', 4"-dihydroxyl, 6-O-methyl, 9-oxime erythromycin A derivative (Compound 5). Compound 5 is then deoximated to yield 6-O-methylerythromycin A (clarithromycin).

The present invention also provides 9-oximesilyl derivatives of erythromycin A, which derivatives are intermediates in the synthesis of 6-O-alkylerythromycin A. A 9-oximesilyl derivative of the present invention can be alkylated or unsubstituded at the 6-position (i.e., 6-OH or 6-O-alkyl), unsubstituted (i.e., 2'-OH, 4"-OH, 3'-dimethyl) or substituted at the 2', 4" or 3'-positions with a conventional protecting group as set forth above.

Thus, in one embodiment, a 9-oximesilyl erythromycin A derivative of the present invention corresponds to the structure I or II.

The following Examples illustrate preferred embodiments of the present invention and are not limiting of the specification and claims in any way.

EXAMPLE 1

Preparation of 2',4"-O-Bis(Trimethylsilyl) Erythromycin A Oxime

To a mixture of 50 grams of erythromycin A oxime and formic acid ($HCO_2H$) in 200 ml of acetonitrile hexamethyidisilazane (HMDS) was added slowly to keep the temperature below 33° C. The mixture was stirred at 28° C. overnight. It was then cooled to about 10° C. and basified with 2N NaOH at a pH of about 10. The product was extracted with heptane, the organic layer was separated, dried over sodium sulfate and then evaporated at reduced pressure to yield 29.5 grams of 2',4"-O-bis(trimethylsilyl) erythromycin A as a white solid. The structure was confirmed by NMR and mass spectra.

EXAMPLE 2

Preparation of 2',4"-O-Bis(Trimethylsilyl) Erythromycin A 9(O-t-Butyldimethylsilyl) Oxime To a solution of 10.7 grams of 2',4"-O-bis(trimethylsilyl) erythromycin A in 25 ml of THF 3.4 ml of triethylamine and 2.17 grams of t-butyldimethylsilyl chloride were added. The mixture was stirred at room temperature overnight. A white solid was precipitated out. The solid was filtered, the filtrate was concentrated under reduced pressure. One hundred ml of water and 200 ml of t-butyl methyl ether were then added to the residue. The mixture was stirred for 5 minutes, the organic layer was separated, dried over $Na_2SO_4$ and concentrated to yield 11.2 grams of 2',4"-O-bis(trimethylsilyl) erythromycin A 9(O-t-butyldimethylsilyl) oxime as a white glassy solid. The structure was confirmed by NMR and mass spectra. $^1$H NMR (500 MHz, CDCl$_3$); δ (ppm)=1.45 (3H,s, 6-CH$_3$), 2.24 [6H, S, N(CH$_3$)$_2$], 3.30 (3H, s, 3"-OCH$_3$). $^{13}$C NMR (CDCl$_3$); δ (ppm)=0.9, 1.0 (2'-OTMS and 4"-OTMS), 40.9 [3'-N(CH$_3$)$_2$], 49.7 (3"-OCH$_3$), 75.5 (6-C), 96.5 (1"-C), 102.5 (1'-C), 175.5, 175.6 (1-C and 9-C). Mass spectrum (FAB): [M+K]$^+$m/z=1045, MW=1006.

EXAMPLE 3

Preparation of 2',4"-O-Bis(Trimethylsilyl) Erythromycin A 9-(O-t-Butyldiphenylsilyl) Oxime To a solution of 10.7 grams of 2',4"-O-bis(trimethylsilyl) erythromycin A in 40 ml of THF 3.4 ml of Et$_3$N and 2.2 grams of t-butyldiphenyl chloride were added. The mixture was stirred at room temperature overnight. HPLC indicated that a small amount of starting material remained. Additional reagents, 1 ml of Et$_3$N and 1 ml of t-butyldiphenyl chloride, were added. The mixture was then heated to 50° C. for 8 hours. The white solid formed was filtered. Forty ml of water and 200 ml of t-butyl methyl ether were added to the filtrate. The mixture was stirred at room temperature for 10 minutes, the organic layer was separated, washed with water, dried over sodium sulfate and concentrated under reduced pressure to yield 11.8 grams of 2',4"-O-bis(trimethylsilyl) erythromycin A 9-(O-t-butyidiphenylsilyl) oxime as a white glassy solid. The structure was confirmed by NMR and mass spectra. $^1$H NMR (400 MHz, CDCl$_3$); δ (ppm)=1.50 (3H,s, 6-CH$_3$), 2.27 [6H, S, N(CH$_3$)$_2$], 3.33 (3H, s, 3"-OCH$_3$), 7.39 ~7.43 (6H, m, Ar), 7.65~7.73 (4H, m, Ar). $^{13}$C NMR (CDCl$_3$); δ (ppm)=0.8, 1.0 (2'-OTMS and 4"-OTMS), 40.9 [3'-N(CH$_3$)$_2$], 49.6 (3"-OCH$_3$), 75.3 (6-C), 96.6 (1"-C), 102.5 (1'-C), 175.4 (9-C), 175.6 (1-C). Mass spectrum (FAB): [M+H]$^+$m/z=1131, MW=1130.

EXAMPLE 4

Preparation of 2',4"-O-Bis(Trimethylsilyl) Erythromycin A 9-(O-Triisopropylsilyl) Oxime To a solution of 10.7 grams of 2', 4"-O-bis(trimethylsilyl) erythromycin A in 40 ml of THF 3.4 ml of Et$_3$N and 3.1 ml of triisopropylsilyl chloride were added. The mixture was stirred at room temperature overnight. Additional reagents, 3.0 ml of Et$_3$N and 3.1 ml of triisopropylsilyl chloride, were added. The mixture was heated to about 50° C. for 4 hours, then stirred overnight at room temperature. The solid formed was filtered, the filtrate was concentrated to give an oil. Forty ml of water and 200 ml of t-butyl methyl ether were added to the oil. The mixture was stirred at room temperature for 10 minutes and the organic layer was separated, washed with water, dried over sodium sulfate and concentrated under reduced pressure to yield 12.7 grams of 2', 4"-O-bis(trimethylsilyl)erythromycin A 9-(O-triisopropylsilyl) oxime as a white glassy solid. The structure was confirmed by NMR and mass spectra. $^1$H NMR (400 MHz, CDCl$_3$); δ (ppm)=1.46 (3H,s, 6-CH$_3$), 2.26 [6H, S, N(CH$_3$)$_2$], 3.29 (3H, s, 3"-OCH$_3$). $^{13}$C NMR (CDCl$_3$); δ (ppm)=0.8, 1.0 (2'-OTMS and 4"-OTMS), 40.9 [3'-N(CH$_3$)$_2$], 49.6 (3"-OCH$_3$), 75.4 (6-C), 96.5 (1"-C), 102.5 (1'-C), 175.1 (9-C), 175.3 (1-C). Mass spectrum (FAB): [M+K]$^+$ m/z=1087, MW =1048.

EXAMPLE 5

Preparation of 2',4"-O-Bis(trimethylsilyl)-6-O-Methylerythromycin A 9-(O-t-Butyidimethylsilyl) Oxime To a ice-cooled solution of 1.0 grams of 2', 4"-O-bis (trimethylsilyl)erythromycin A 9(O-t-butyidimethylsilyl) oxime in 10 ml of dimethyl sulfoxide and tetrahydrofuran (1:1 mixture) 0.12 ml of methyl iodide and 80 mg of 60% sodium hydride were added. The mixture was stirred at about 5° C. for 2 hours. One ml of 50% aqueous dimethylamine solution was added to the reaction solution. The mixture was stirred for 10 minutes and was then poured into 20 ml of saturated sodium chloride solution. The product was extracted with t-butyl methyl ether and the organic layer was separated, washed with a saturated sodium chloride solution, dried over Na$_2$SO$_4$, and concentrated under reduced pressure to give a crude product. The crude product was dissolved in a mixture of 20 ml of hexane and 10 ml of acetonitrile. The upper hexane layer was separated and concentrated under reduced pressure to yield 680 mg of 2', 4"-O-bis(trimethylsilyl)-6-O-methylerythromycin A 9-(O-t-butyidimethylsilyl) oxime which was used in the desilylation step without further purification. Mass spectrum (FAB) :[M+H]$^+$m/z=1021, MW=1020.

EXAMPLE 6

Preparation of 2',4"-O-Bis(trimethylsilyl)-6-O-Methylerythromycin A 9(O-t-Butyldiphenylsilyl) Oxime To an ice-cooled solution of 1.13 grams of 2',4"-O-bis (trimethylsilyl)erythromycin A 9(O-t-butyldiphenylsilyl) oxime in 10 ml of dimethyl sulfoxide and tetrahydrofuran (1:1 mixture) 0.12 ml of methyl iodide and 80 mg of 60% sodium hydride were added. The mixture was stirred at about 5° C. for 2 hours. One ml of 50% aqueous dimethylamine solution was added to the reaction solution. The mixture was stirred for 10 minutes and was then poured into 20 ml of saturated sodium chloride solution. The product was extracted with t-butyl methyl ether and the organic layer was separated and washed with a saturated sodium chloride solution. It was then dried over Na$_2$SO$_4$ and concentrated under reduced pressure to give a crude product. The crude product was dissolved in a mixture of 20 ml of hexane and 10 ml of acetonitrile. The upper hexane layer was separated and concentrated under reduced pressure to yield 858 mg of 2',4"-O-bis(trimethylsilyl)-6-O-methylerythromycin A 9-(O-t-butyldiphenylsilyl) oxime which was used in the desilylation step without further purification. The product can be further purified by recrystallization from MeOH. Mass spectrum (FAB): [M+H]$^+$m/z=1145, MW=1144.

EXAMPLE 7

Preparation of 2',4"-O-Bis(Trimethylsilyl)-6-O-Methylerythromycin A 9-(O-t-Butyidiphenylsilyl) Oxime To an ice-cooled solution of 1.13 grams of 2',4"-O-bis (trimethylsilyl)erythromycin A 9(O-t-butyldiphenylsilyl) oxime in 10 ml of dimethyl sulfoxide and tetrahydrofuran (1:1 mixture) 0.12 ml of methyl 128 mg of powdered potassium hydroxide were added. The mixture was stirred at about 5° C. for 1.5 hours. One ml of 50% aqueous dimethylamine solution was added to the reaction solution. The mixture was stirred for 10 minutes and then poured into 20 ml of saturated sodium chloride solution. The product was extracted with t-butyl methyl ether and the organic layer was washed with a saturated sodium chloride solution. It was then dried over Na$_2$SO$_4$ and concentrated under reduced pressure to give a crude product. The crude product was dissolved in a mixture of 20 ml of hexane and 10 ml of acetonitrile. The upper hexane layer was separated and concentrated under reduced pressure to yield 805 mg of 2',4"-O-bis(trimethylsilyl)-6-O-methylerythromycin A 9-(O-t-butyldiphenylsilyl) oxime which was used in the desilylation step without further purification. The product can be further purified by recrystallization from MeOH. Mass spectrum (FAB): [M+H]$^+$m/z=1145, MW=1144.

EXAMPLE 8

Preparation of 2',4"-O-Bis(trimethylsilyl)-6-O-Methylerythromycin A 9-(O-Triisopropylsilyl) Oxime To an ice-cooled solution of 1.05 grams of 2',4"-O-bis(trimethylsilyl)erythromycin A 9(O-triisopropylsilyl) oxime in 10 ml of dimethyl sulfoxide and tetrahydrofuran (1:1 mixture) 0.12 ml of methyl iodide and 80 mg of 60% of sodium hydroxide were added. The mixture was stirred at about 5° C. for 2.0 hours. One ml of 50% aqueous dimethylamine solution was added to the reaction solution. The mixture was stirred for 10 minutes and then poured into 20 ml of saturated sodium chloride solution. The product was extracted with t-butyl methyl ether and the organic layer was washed with a saturated sodium chloride solution. It was then dried over $Na_2SO_4$ and concentrated under reduced pressure to give a crude product. The crude product was dissolved in a mixture of 20 ml of hexane and 10 ml of acetonitrile. The upper hexane layer was separated and concentrated under reduced pressure to yield 810 mg of 2',4"-O-bis(trimethylsilyl)-6-O-methylerythromycin A 9-(O-triisopropylsilyl) oxime which was used in the desilylation step without further purification. The product can be further purified by recrystallization from MeOH. The structure was confirmed by NMR and mass spectra. $^1$H NMR (400 MHz, CDCl$_3$); δ (ppm)=1.47 (3H,s, 6-CH$_3$), 2.27 [6H, S, N(CH$_3$)$_2$], 3.11 (3H, s, 6-OCH$_3$), 3.32 (3H, s, 3"-OCH$_3$). $^{13}$C NMR (CDCl$_3$); δ (ppm)=0.8, 1.1 (2'-OTMS and 4"-OTMS), 40.9 [3'-N(CH$_3$)$_2$], 49.7 (3"-OCH$_3$), 51.2 (6-OCH$_3$), 78.9 (6-C), 96.2 (1"-C), 102.5 (1'-C), 174.3 (9-C), 175.9 (1-C). Mass spectrum (FAB): [M+H]$^+$m/z= 1163, MW =1062.

EXAMPLE 9

Preparation of 2',4"-O-Bis(trimethylsilyl)-6-O-Methylerythromycin A 9-(O-Triisopropylsilyl) Oxime To an ice-cooled solution of 1.05 grams of 2',4"-O-bis(trimethylsilyl)erythromycin A 9(O-triisopropylsilyl) oxime in 10 ml of dimethyl sulfoxide and tetrahydrofuran (1:1 mixture) 0.12 ml of methyl iodide and 128 mg of powdered potassium hydroxide were added. The mixture was stirred at about 5° C. for 1.5 hours. One ml of 50% aqueous dimethylamine solution was added to the reaction solution. The mixture was stirred for 10 minutes and then poured into 20 ml of saturated sodium chloride solution. The product was extracted with t-butyl methyl ether and the organic layer was washed with a saturated sodium chloride solution, dried over $Na_2SO_4$ and concentrated under reduced pressure to give a crude product. The crude product was dissolved in a mixture of 20 ml of hexane and 10 ml of acetonitrile. The upper hexane layer was separated and concentrated under reduced pressure to yield 805 mg of 2',4"-O-bis(trimethylsilyl)-6-O-methylerythromycin A 9(O-triisopropylsilyl) oxime which was used in the desilylation step without further purification. The product can be further purified by recrystallization from MeOH. The structure was confirmed by NMR and mass spectra. $^1$H NMR (400 MHz, CDCl$_3$); δ (ppm)=1.47 (3H,s, 6-CH$_3$), 2.27 [6H, S, N(CH$_3$)$_2$], 3.11 (3H, s, 6-OCH$_3$), 3.32 (3H, s, 3"-OCH$_3$). $^{13}$C NMR (CDCl$_3$); δ (ppm)=0.8, 1.1 (2'-OTMS and 4"-OTMS), 40.9 [3'-N(CH$_3$)$_2$], 49.7 (3"-OCH$_3$), 51.2 (6-OCH$_3$), 78.9 (6-C), 96.2 (1"-C), 102.5 (1'-C), 174.3 (9-C), 175.9 (1-C). Mass spectrum (FAB): [M+H]$^+$m/z=1163, MW =1062.

EXAMPLE 10

Preparation of 6-O-Methylerythromycin Oxime

To a solution of 400 mg of 2',4"-O-bis(trimethylsilyl)-6-O-methylerythromycin A 9(O-t-butyldiphenylsilyl) oxime in 5 ml of isopropyl alcohol 5 ml of water and 10 drops of formic acid were added. The solution was stirred at room temperature for 20 minutes and then basified with a 2N sodium hydroxide solution to a pH of about 10. The product was extracted with isopropyl acetate. The organic layer was separated, dried over sodium sulfate and concentrated under reduced pressure to yield 231 grams of 6-O-methylerythromycin oxime as a white solid, which can be recrystallized from EtOH/Hexane. Mass spectrum: MW=762.

EXAMPLE 11

Preparation of 6-O-Methylerythromycin Oxime

To a solution of 3 grams of 2',4"-O-bis(trimethylsilyl)-6-O-methylerythromycin A 9(O-triisopropylsilyl) oxime in 10 ml of tetrahydrofuran 15 ml of a 1M solution of tetrabutylammonium fluoride were added. The resulting solution was stirred at room temperature for ½ hour. Ten ml of water were then added to this solution. Tetrahydrofuran was removed under reduced pressure and the product was extracted with isopropyl acetate. The organic layer was separated, dried over sodium sulfate and concentrated under reduced pressure to give the crude product, which was crystallized from EtOH / Hexane to give 600 mg of 6-O-methylerythromycin oxime as a white solid. The structure was confirmed by NMR and mass spectra. $^1$H NMR (400 MHz, CDCl$_3$); δ (ppm)=1.48 (3H,s, 6-CH$_3$), 2.29 [6H, S, N(CH$_3$)$_2$], 3.10 (3H, s, 6-OCH$_3$), 3.33 (3H, s, 3"-OCH$_3$). $^{13}$C NMR (CDCl$_3$); δ (ppm)=40.3 [3'-N(CH$_3$)$_2$], 49.5 (3"-OCH$_3$), 51.2 (6-OCH$_3$), 78.7 (6-C), 96.0 (1"-C), 102.8 (1'-C), 170.5 (9-C), 175.7 (1-C). Mass spectrum (DCI): [M+H]$^+$m/z=763, MW=762.

What is claimed is:

1. A process of preparing a 6-O-alkylerythromycin A derivative comprising silylating a 9-oxime erythromycin A derivative to form a 9-oximesilyl erythromycin A derivative and reacting the 9-oximesilyl erythromycin A derivative with an alkylating agent.

2. The process of claim 1 wherein silylating is accomplished by reacting the 9-oxime erythromycin A derivative with a silylating agent of the formula:

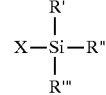

where R', R", and R'" are independently hydrogen, lower alkyl, aryl, phenyl, phenyl substituted lower alkyl, cycloalkyl or alkenyl and X is a halogen or a sulfonate.

3. The process of claim 1 wherein the 9-oxime erythromycin A derivative has a protecting group in place of (a) the hydrogen of the 2'-hydroxyl group, (b) the hydrogen of the 4"-hydroxyl group, (c) a methyl group of the 3'-dimethylamino group, (d) hydrogens of the 2'-hydroxyl group and the 4"-hydroxyl group, (e) a methyl group of the 3'-dimethylamino group and one of the hydrogens of the 2'- or 4"-hydroxyl groups, or (f) a methyl group of the 3'-dimethylamino group and both of the hydrogens of the 2'- and 4"-hydroxyl groups.

4. The process of claim 1 wherein the 9-oxime erythromycin A derivative has (a) a O-protecting group in place of the hydrogen of the 2'-hydroxyl group; (b) a conventional O-protecting group in place of the hydrogen of the 4"-hydroxyl group; (c) a conventional O-protecting group in place of both of the hydrogens of the 2'-hydroxyl group and the 4"-hydroxyl group; (d) the 3'-dimethylamino group protected as a quaternary salt with a 2-alkenyl group, benzyl group or substituted benzyl group; (e) the 3'-dimethylamino group protected as a quaternary salt with a 2-alkenyl group, benzyl group or substituted benzyl group and a conventional O-protecting group in place of one of the hydrogens of the 2'- or 4"-hydroxyl groups; or (f) the 3'-dimethylamino group protected as a quaternary salt with a 2-alkenyl group, benzyl group or substituted benzyl group and a conventional O-protecting group in place of both of the hydrogens of the 2'- and 4"-hydroxyl groups.

5. The process of claim 1 wherein the 9-oximesilyl erythromycin A derivative has the structure I, below:

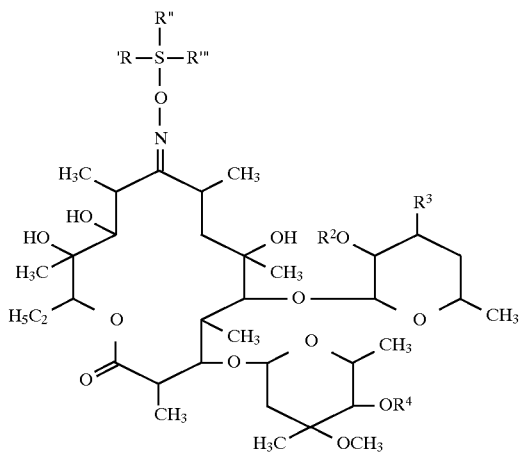

where R', R"and R'" are each independently hydrogen, lower alkyl, aryl, phenyl, phenyl substituted lower alkyl, cycloalkyl or alkenyl; $R^2$ and $R^4$ are each independently hydrogen, silyl, alkylcarbonyl, alkoxycarbonyl, acyl, lower alkenyl monocarbonyl, lower alkoxycarbonylalkylcarbonyl or arylcarbonyl; and $R^3$ is —$NR^5(CH_3)_2$, where $R^5$ is methyl ($CH_3$) or a N-protecting group or —$N^+(CH_3)_2R^6X$, where $R^6$ is 2-alkenyl, benzyl or substituted benzyl, and X is a halogen such as Br, Cl or I, with the proviso that at least one of $R^2$ and $R^4$ is not hydrogen.

6. The process of claim 3 wherein $R^3$ is —$N(CH_3)_2$ and $R^2$ and $R^4$ are both:

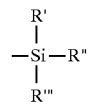

7. A compound having the structure II below:

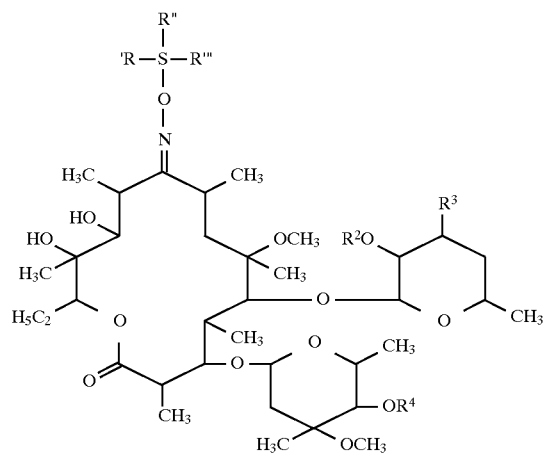

where R', R"and R'" are each independently hydrogen, lower alkyl, aryl, phenyl, phenyl substituted lower alkyl, cycloalkyl or alkenyl; $R^2$ and $R^4$ are each independently hydrogen, silyl, alkoxycarbonyl, alkylcarbonyl, acyl, lower alkenyl monocarbonyl, lower alkoxycarbonylalkylcarbonyl or arylcarbonyl; and $R^3$ is —$NR^5(CH_3)_2$, where $R^5$ is methyl ($CH_3$) or a N-protecting group or —$N^+(CH_3)_2R^6X$, where $R^6$ is 2-alkenyl, benzyl or substituted benzyl, and X is Br, Cl or I.

8. A compound having the structure I below:

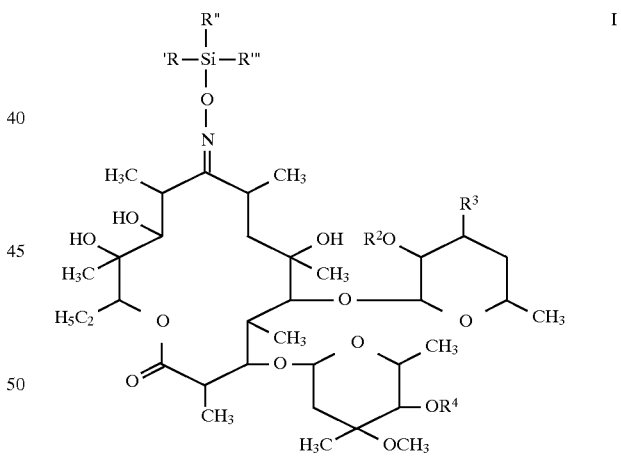

where R', R"and R'" are each independently hydrogen, lower alkyl, aryl, phenyl, phenyl substituted lower alkyl, cycloalkyl or alkenyl; $R^2$ and $R^4$ are each independently hydrogen, silyl, alkoxycarbonyl, alkylcarbonyl, acyl, lower alkenyl monocarbonyl, lower alkoxycarbonylalkylcarbonyl or arylcarbonyl; and $R^3$ is —$NR^5(CH_3)_2$, where $R^5$ is methyl ($CH_3$) or a N-protecting group or —$N^+(CH_3)_2R^6X$, where $R^6$ is 2-alkenyl, benzyl or substituted benzyl, and X is Br, Cl or I.

9. A process of preparing 6-O-alkylerythromycin A comprising deoximating an erythromycin A 9-oximesilyl, 6-O-alkyl derivative prepared by the process of claim 1.

* * * * *

UNITED STATES PATENT AND TRADEMARK OFFICE
CERTIFICATE OF CORRECTION

PATENT NO. : 5,837,829
DATED : Nov. 17, 1998
INVENTOR(S) : Ku

It is certified that error appears in the above-identified patent and that said Letters Patent is hereby corrected as shown below:

Column 13, line 34, change "S"

to --Si--.

Column 14, line 10, change "S"

to --Si--.

Signed and Sealed this

Sixteenth Day of November, 1999

Attest:

Q. TODD DICKINSON

*Attesting Officer*     *Acting Commissioner of Patents and Trademarks*